(12) United States Patent
Dangerfield et al.

(10) Patent No.: US 9,919,046 B2
(45) Date of Patent: Mar. 20, 2018

(54) POST RELEASE MODIFICATION OF VIRAL ENVELOPES

(71) Applicant: VIN DE BONA TRADING CO. PTE LTD, Singapore (SG)

(72) Inventors: John Dangerfield, Singapore (SG); Christoph Metzner, Wiener Neustadt (AT)

(73) Assignee: VIN DE BONA TRADING CO. PTE LTD, Singapore (SG)

(*) Notice: Subject to any disclaimer, the term of this patent is extended or adjusted under 35 U.S.C. 154(b) by 0 days.

(21) Appl. No.: 14/860,107

(22) Filed: Sep. 21, 2015

(65) Prior Publication Data

US 2016/0206730 A1 Jul. 21, 2016

Related U.S. Application Data

(63) Continuation of application No. 12/988,046, filed as application No. PCT/EP2009/054016 on Apr. 3, 2009, now Pat. No. 9,139,817.

(30) Foreign Application Priority Data

Apr. 17, 2008 (EP) .................... 08154748

(51) Int. Cl.
   - A61K 39/265 (2006.01)
   - C12N 7/00 (2006.01)
   - C12Q 1/04 (2006.01)
   - A61K 39/00 (2006.01)

(52) U.S. Cl.
   CPC .............. *A61K 39/265* (2013.01); *C12N 7/00* (2013.01); *C12Q 1/04* (2013.01); *A61K 2039/525* (2013.01); *C12N 2710/16734* (2013.01); *C12N 2710/16751* (2013.01); *C12N 2740/10043* (2013.01); *C12N 2740/15043* (2013.01)

(58) Field of Classification Search
   None
   See application file for complete search history.

(56) References Cited

U.S. PATENT DOCUMENTS 6,235,483 B1  5/2001  Wolber et al.

FOREIGN PATENT DOCUMENTS

| WO | 9309221 A1 | 5/1993 |
|----|------------|--------|
| WO | 0017374 A1 | 3/2000 |
| WO | 2005118802 A2 | 12/2005 |

OTHER PUBLICATIONS

Kueng et al., Journal of Virology, 2007, 81(16):8666-8676.*
Legler et al., The FASEB Journal, Jan. 2005, 19(1):73-75.*
Aloia et al., "Lipid composition and fluidity of the human immunodeficiency virus envelope and host cell plasma membranes", Proc. Natl. Acad. Sci. USA, 90:5181-5185, 1993.
Pessin et al., "Budding of Rous Sarcoma Virus and Vesicular Stomatitis Virus from Localized Lipid Regionsi n the Plasma Membrane of Chicken Embryo Fibroblasts*", The Journal of Biological Chemistry, 256(19):9044-9050, 1980.
Shaw et al., "Cellular Proteins in Influenza Virus Particles", PLoS Pathog 4(6): e1000085. doi:10.1371/journal.ppat.1000085, 2008.
Sullivan-Tailyour et al., "Plasma Membrane Proteins and Glycoproteins Induced by Human Cytomegalovirus nfection of Human Embryonic Fibroblasts", J. gen. Virol., 67:515-526, 1986.
Accession No. P13987, CD59_HUMAN in UniProtKB/Swiss-Prot, integrated in Jan. 1, 1990. Accessed online Jan. 27, 2011 at http://www.uniprot.org/uniprot/P13987#section_general—10 pages.
Beer et al., Amphotropic murine leukaemia virus envelope protein is associated with cholesterol-rich microdomains. Virol J. Apr. 19, 2005;2:36 (9 pages).
Breun et al., Protection of MLV Vector Particles from Human Complement. Biochem Biophys Res Commun. Oct. 14, 1999;264(1):1-5.
Brugger et al., Human Immunodeficiency Virus Type 1 Nef protein modulates the lipid composition of virions and host cell membrane microdomains. Retrovirology. Oct. 1, 2007;4:70 (12 pages).
Campbell et al., A monomeric red fluorescent protein. Proc Natl Acad Sci U S A. Jun. 11, 2002;99(12):7877-7882.
Campbell, Unit Three: The Gene.in Biology. Redwood City, CA: Benjamin/Cummings Publishing Company, Inc., 1993:350-351 (4 pages total).
Chan et al., Conjugation of Lentivirus to Paramagnetic Particles via Nonviral Proteins Allows Efficient Concentration and Infection of Primary Acute Myeloid Leukemia Cells. J Virol. Oct. 2005;79(20):13190-13194 . _.
Hlavaty et al., Multiple Modifications Allow High-Titer Production of Retroviral Vectors Canying Heterologous Regulatory Elements. J Virol. Feb. 2004;78(3):1384-1392.
Ikeda et al., Continuous high-titer HIV-1 vector production. Nat Biotechnol. May 2003;21(5):569-572.
Ito et al., Medical Application of Functionalized Magnetic Nanoparticles. J Biosci Bioeng. Jul. 2005;100(1):1-11.
Jordan et al., The effect of thermotherapy using magnetic nanoparticles on rat malignant glioma. J Neurooncol. May 2006;78(1):7-14.
Keler et al., Antibody-targeted vaccines. Oncogene. May 28, 2007;26(25):3758-3767.

(Continued)

*Primary Examiner* — Stacy B Chen
(74) *Attorney, Agent, or Firm* — Acuity Law Group, PC; Michael A. Whittaker

(57) ABSTRACT

Disclosed are methods of treatment of a subject, such as a method of vaccination, immunomodulation or gene therapy of a subject. These methods comprise administering to the subject a modified enveloped viral particle, wherein the modified enveloped viral particle has been obtained by a method comprising the steps of a) incubating a fluid containing enveloped viral particles with one or more reactants consisting of a hydrophilic target domain and a lipophilic membrane anchor domain, wherein the lipophilic membrane anchor domain becomes integrated into the lipid double layer of the envelope of the viral particle, wherein the hydrophilic target domain becomes exposed to the fluid; and b) separating enveloped modified viral particles from excessive reactants.

16 Claims, 7 Drawing Sheets

(56) References Cited

OTHER PUBLICATIONS

Figure 2A:
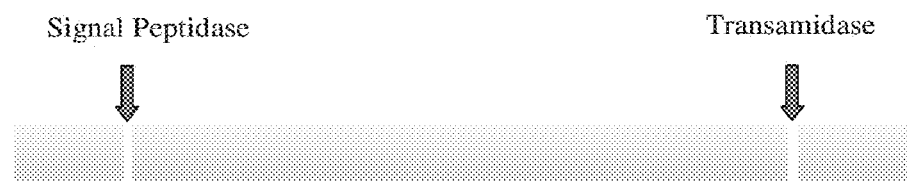

Klein et al., Rapid identification of viable retrovirus-transduced cells using the green fluorescent protein as a marker. Gene Ther. Nov. 1997;4(11):1256-1260.
Lim et al., Immobilization of histidine-tagged proteins by magnetic nanoparticles encapsulated with nitrilotriacetic acid (NTA)-phospholipids micelle. Biochem Biophys Res Commun. Jun. 9, 2006;344(3):926-930.
McHugh et al., Construction, purification, and functional incorporation on tumor cells of glycolipid-anchored human B7-1 (CD80). Proc Natl Acad Sci U S A. Aug. 15, 1995;92(17):8059-8063.
Medof et al., Cell-surface engineering with GPI-anchored proteins. FASEB J. Apr. 1996;10(5):574-586.
Metzner et al., Association of glycosylphosphatidylinositol-anchored protein with retroviral particles. FASEB J. Aug. 2008;22(8):2734-2739.
Metzner et al., Rafts, anchors and viruses—A role for glycosylphosphatidylinositol anchored proteins in the modification of enveloped viruses and viral vectors. Virology. Dec. 20, 2008;382(2):125-131.
Morandat et al., Cholesterol-dependent insertion of glycosylphosphatidylinositol-anchored enzyme. Biochim 3iophys Acta. Aug. 31, 2002;1564(2):473-478.
Pambalk et al., Specific packaging of spliced retroviral vector transcripts lacking the Psi-region. Biochem Biophys Res Commun. Apr. 26, 2002;293(1):239-246.
Paulick et al., Synthetic Analogues of Glycosylphosphatidylinositol-Anchored Proteins and Their Behavior in Supported Lipid Bilayers. J Am Chem Soc. Sep. 19, 2007;129(37):11543-11550.
Premkumar et al., Properties of Exogenously Added GPI-Anchored Proteins Following Their Incorporation Into cells. J Cell Biochem. 2001;82(2):234-245.
Rohrbach et al., Targeted Delivery of the ErbB2/HER2 Tumor Antigen to Professional APCs Results in Effective Antitumor Immunity. J Immunol. May 1, 2005;174(9):5481-5489.
Ronzon et al., Insertion of a Glycosylphosphatidylinositol-Anchored Enzyme into Liposomes. J Membr Biol. Feb. 1, 2004;197(3):169-177.
Roux et al., A versatile and potentially general approach to the targeting of specific cell types by retroviruses: application to the infection of human cells by means of major histocompatibility complex class I and class II antigens by mouse ecotropic murine leukemia virus-derived viruses. Proc Natl Acad Sci U S A. Dec. 1989;86(23):9079-9083.
Saifuddin et al., Human immunodeficiency virus type 1 incorporates both glycosyl phosphatidylinositol-anchored CD55 and CD59 and integral membrane CD46 at levels that protect from complement-mediated destruction. J Gen Virol. Aug. 1997;78 ( Pt 8):1907-1911.
Schevchenko et al., Mass Spectrometric Sequencing of Proteins from Silver-Stained Polyacrylamide Gels. Anal Chem. Mar. 1, 1996;68(5):850-858.
Skountzou et al., Incorporation of Glycosylphosphatidylinositol-Anchored Granulocyte- Macrophage Colony-Stimulating Factor or CD40 Ligand Enhances Immunogenicity of Chimeric Simian Immunodeficiency Virus-Like Particles. J Virol. Feb. 2007;81(3):1083-1094.
Steinrigl et al., Mutations in the catalytic core or the C-terminus of murine leukemia virus (MLV) integrase disrupt virion infectivity and exert diverse effects on reverse transcription. Virology. May 25, 2007;362(1):50-59.
Taraboletti et al., Bioavailability of VEGF in Tumor-Shed Vesicles Depends on Vesicle Burst Induced by Acidic pH1. Neoplasia. Feb. 2006;8(2):96-103.
Wilhelm et al., Tumour Cell Toxicity of Intracellular Hyperthermia Mediated by Magnetic Nanoparticles. J Nanosci Nanotechnol. Aug. 2007;7(8):2933-2937.
Yang et al., Gamma-Retroviral Vectors Enveloped with an Antibody and an Engineered Fusogenic Protein Achieved Antigen-Specific Targeting. Biotechnol Bioeng. Oct. 1, 2008;101(2):357-368.
Yang et al., Targeting lentiviral vectors to specific cell types in vivo. Proc NaTl Aced Sci U S A. Aug. 1, 2006;103(31):11479-11484.
Yang et al., Engineered Lentivector Targeting of Dendritic Cells for in Vivo Immunization. Nat Biotechnol. Mar. 26, 2008(3):326-334.
Zacharias et al., Partitioning of Lipid-Modified Monomeric GFPs into Membrane Microdomains of Live Cells. Science. May 3, 2002;296(5569):913-916.
Acharias, Sticky Caveats in an Otherwise Glowing Report: Oligomerizing Fluorescent Proteins and Their Use in Cell Biology. Sci STKE. May 7, 2002;2002(131):pe23.
Ziegler et al., Targeting Lentiviral Vectors to Antigen-Specific Immunoglobulins. Hum Gene Ther. Sep. 2008;19(9):861-872.

* cited by examiner

FIG. 1A
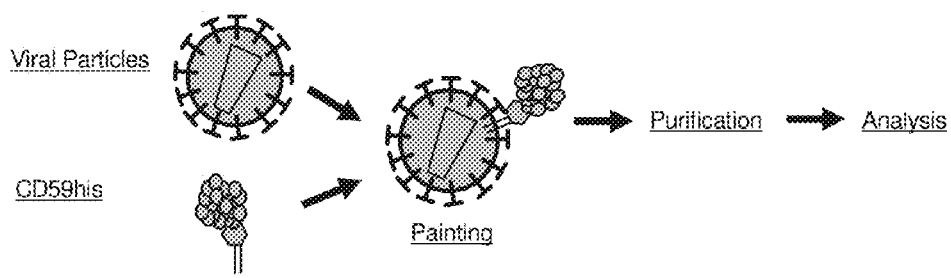
FIG. 1B
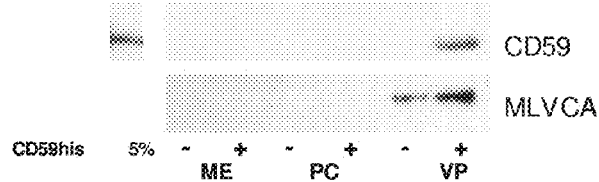
FIG. 1C
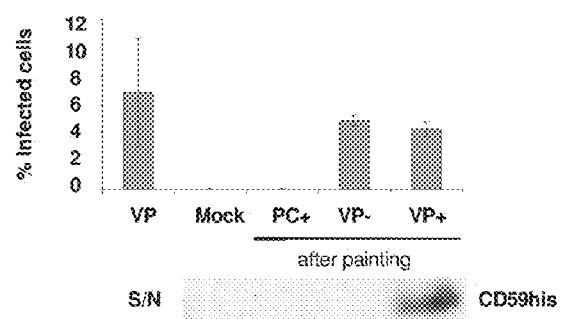
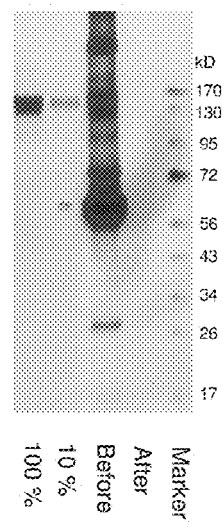
FIG. 1D

SEQUENCE LISTING

<160> NUMBER OF SEQ ID NOS: 8

<210> SEQ ID NO 1
<211> LENGTH: 40
<212> TYPE: DNA
<213> ORGANISM: Artificial Sequence
<220> FEATURE:
<223> OTHER INFORMATION: MEHindIIIF primer

<400> SEQUENCE: 1
cgcgcgcaag cttaatcaaa acatggctca gcggatgaca                40

<210> SEQ ID NO 2
<211> LENGTH: 45
<212> TYPE: DNA
<213> ORGANISM: Artificial Sequence
<220> FEATURE:
<223> OTHER INFORMATION: MonoHisEG3R primer

<400> SEQUENCE: 2
gtggtggtga tggtggtgct tgtacagctc gtccatgccg agagt           45

<210> SEQ ID NO 3
<211> LENGTH: 39
<212> TYPE: DNA
<213> ORGANISM: Artificial Sequence
<220> FEATURE:
<223> OTHER INFORMATION: HisEG1F primer

<400> SEQUENCE: 3
caccaccatc accaccaccc aaataaagga agtggaacc                 39

<210> SEQ ID NO 4
<211> LENGTH: 29
<212> TYPE: DNA
<213> ORGANISM: Artificial Sequence
<220> FEATURE:
<223> OTHER INFORMATION: EGApaIR primer

<400> SEQUENCE: 4
gaatagggcc ctaagtcagc aagcccatg                            29

<210> SEQ ID NO 5
<211> LENGTH: 44
<212> TYPE: DNA
<213> ORGANISM: Artificial Sequence
<220> FEATURE:
<223> OTHER INFORMATION: CD59(2)FKHindIII primer

<400> SEQUENCE: 5
cacgacaagc ttaccatggg aatccaagga gggtctgtcc tgtt            44

<210> SEQ ID NO 6
<211> LENGTH: 43
<212> TYPE: DNA
<213> ORGANISM: Artificial Sequence
<220> FEATURE:
<223> OTHER INFORMATION: CD59(2)RApaI primer

<400> SEQUENCE: 6
atgacgggcc cttagggatg aaggctccag gctgctgcca gaa             43

<210> SEQ ID NO 7
<211> LENGTH: 40
<212> TYPE: DNA
<213> ORGANISM: Artificial Sequence

```
<220> FEATURE:
<223> OTHER INFORMATION: CD59FHis primer

<400> SEQUENCE: 7
catcaccatc accatcacct gcagtgctac aactgtccta                                        40

<210> SEQ ID NO 8
<211> LENGTH: 40
<212> TYPE: DNA
<213> ORGANISM: Artificial Sequence
<220> FEATURE:
<223> OTHER INFORMATION: CD59RHis primer

<400> SEQUENCE: 8
gtgatggtga tggtgatggc tatgacctga atggcagaag                                        40
```

POST RELEASE MODIFICATION OF VIRAL ENVELOPES

CROSS-REFERENCE TO RELATED PATENT APPLICATIONS

This application is a continuation application of U.S. patent application Ser. No. 12/988,046 filed Oct. 15, 2010, now U.S. Pat. No. 9,139,817, issued Sep. 22, 2015, which is the United States national stage patent application of International Application No. PCT/EP2009/054016, filed Apr. 3, 2009, which claims the benefit of priority of European patent application EP 08154748.1 filed Apr. 17, 2008, the contents of each of which are hereby incorporated by reference it their entirety for all purposes.

SEQUENCE LISTING

The instant application contains a Sequence Listing which has been submitted in ASCII format via EFS-Web and is hereby incorporated by reference in its entirety. Said ASCII copy, created on Sep. 21, 2015, is named SCH2500CT_SeqListing.txt and is 2 kilobytes in size.

FIELD OF THE INVENTION

The present invention relates to enveloped virus particles providing an altered composition of viral envelopes, methods and means for exogenously altering the composition of viral envelopes by anchoring of substances into viral membranes, pharmaceutical compositions and the use of such altered enveloped virus particles.

BACKGROUND OF THE INVENTION

Cholesterol-rich microdomains like rafts and caveolae are specialized regions of the plasma membrane and play an important role for several cellular processes e.g. signal transduction, and for the life cycle of certain viruses (e.g., the entry and exit steps). These domains are enriched in cholesterol, sphingomyelin, ganglioside GM1 and caveolin proteins. The cholesterol molecules are intercalated between the lipid acyl chains and cause a decrease of the fluidity of these membrane regions leading to their resistance against treatment with non-ionic detergents like Triton X-100. Therefore, these regions are also referred to as detergent resistant microdomains (DRMs). The specific lipid composition of DRMs leads to the selective incorporation and concentration of specific cellular proteins. Such proteins often exhibit Glycosylphosphatidylinositol (GPI) anchoring and fatty acylation.

It is known that viral proteins of certain viruses e.g. the envelope protein (Env) of the ecotropic murine leukemia virus (E-MLV) or of the human immunodeficiency virus type 1 (HIV-1) associate with DRMs after transport to the plasma membrane. Similarly, Gag proteins of HIV-1 prefer DRMs as cellular destinations after synthesis in the cytoplasm. Mutations of HIV-1 Env or E-MLV Env palmitoylation sites or the HIV-1 Gag myristoylation site impair the association of these proteins with DRMs. Knock out of Env palmitoylation sites led to a decreased viral titer due to a reduced Env incorporation into the viral particles.

Therefore, DRMs enriched in viral capsid and envelope proteins are considered to be platforms for assembly and budding of viruses from infected cells.

The virus envelope consists of envelope proteins (Env) embedded in a membrane consisting of a lipid double layer, whereas the viral membrane composition resembles the lipid composition of DRMs and differs from the average distribution of lipids in the plasma membrane of the host cell.

It is also known that the viral envelope may also contain cellular proteins picked up from the virus producing cell during the budding process. This has been used to incorporate specific membrane proteins e.g. complement inhibitors like CD59 (WO 00/17374) into envelops of viral particles making use of the natural transport pathway of the host cell.

Recently such approaches have also been used to increase the immunogenicity of simian immunodeficiency virus (SIV) based virus-like particles (VLPs) by addition of CD40 ligand and granulocyte-macrophage colony-stimulating factor (GM-CSF) or to modify murine leukaemia virus (MLV) based VLPs with cytokines such as IL-4 to induce differentiation of monocytes, or IL-2 to induce proliferation of peripheral blood mononuclear cells (PBMCs).

Modification of retroviral vectors so far depends on the genetic engineering of virus producer cell lines by transfection. Such an approach is very inconvenient and time consuming, because for each component to be inserted into viral envelops the respective host cell has to be genetically modified. Such an approach is also limited to proteins and polypeptides which have to be synthesized by the host cell and transported to the plasma membrane.

A typical cellular transport pathway makes use of a Glycosylphosphatidylinositol (GPI) anchor to direct proteins and polypeptides to the outer leaflet of cell membranes. Glycosylphosphatidylinositol (GPI) anchors are attached to protein precursors at the endoplasmatic reticulum (ER) membrane by a transamidase enzyme complex and delivered to the outer leaflet of the plasma membrane. GPI-linked proteins serve different functions i.e. in the regulation of complement activity (CD59; CD55) or as hydrolytic enzymes (e.g. alkaline phosphatase and renal dipeptidase). GPI anchors consist of a hydrophilic oligosaccharide and a lipophilic fatty acid part.

It was already demonstrated that the lipophilic part of said GPI anchors may mediate the exogenous insertion of proteins into lipid membranes of cells (Medof (1996); Legler (2005); McHugh (1995); Premukar (2001) and artificial lipid membranes (Ronzon (2004); Morandar (2002)) which are generally characterized by a low protein content in relation to the fatty acid content. The process of insertion of substances like proteins is termed "painting" (Medof (1996)). It has further been demonstrated that GPI anchors can be added to previously non-GPI-linked proteins (e.g. green fluorescent protein (GFP) by genetically addition of a GPI signaling sequence (GSS) to their C-terminal end and that these proteins retain their biological functions (McHugh (1995); Premukar (2001); Legler 2005).

In contrast to artificial or cellular membranes the amount of viral envelope proteins in virions is extremely high so that the lipids of the virus envelope are completely shadowed making viruses e.g. highly resistant to detergents and environmental influences. Typical lipid to protein mol fractions in cell membrane expressed as mole percentage (mol %) are 80:20 or higher whereas in typical viral envelopes the ratio is 30:70 or less (M. K. Jain, R. C. Wagner: Introduction to Biological Membranes, New York (Whiley) 1980, ISNB 0471034711). The accessibility of the virus membrane lipid layer is drastically reduced which makes it unlikely to insert voluminous proteins or other voluminous target domains into the viral envelope after release of the virus from its host cell. While trying to generate more efficient therapeutic viral vectors for gene therapy the inventors developed methods for an easier and more rapid anchoring of substances into membranes of enveloped viruses, especially in order to provide a quick and flexible alternative to engineering of genetically modified virus producing cell lines.

It was absolutely unexpected and surprising for the inventors that compounds, especially proteins linked to membrane anchor domains like Glycosylphosphatidylinositol (GPI) anchors can successfully be inserted into lipid double layers of viral envelopes when added exogenously to isolated viral particles resulting in viral particles with altered surface characteristics. The method presented herein is useful for generation of virus particles with well designed chemical and biological characteristics depending on the target domains inserted.

DETAILED DESCRIPTION OF THE INVENTION

The terms "virus", "virion" and "viral particle" are used interchangeably. A virus is a sub-microscopic infectious agent that is unable to grow or reproduce outside a host cell. Each virus consists of genetic material, DNA or RNA, within a protective protein coat called a capsid. The capsid shape varies from simple helical and icosahedral (polyhedral or near-spherical) forms, to more complex structures with tails or an envelope. In the context of the present invention only enveloped virions are considered. Viruses infect cellular life forms and are grouped into animal, plant and bacterial types, according to the type of host infected. For working of the invention the genetic information of the viral particle is not relevant. Therefore, the present invention comprises wild-type viruses as well as genetically modified viral vectors which can be replication competent or incompetent.

The viral vector may additionally or alternatively contain modifications to its natural viral envelope e.g. by genetically modification of the viral genome to produce e.g. chimeric envelope proteins or by making use of packaging cell lines for pseudo typing, as used for infection retargeting and/or capping proteins, as used to prevent infection or to limit it to certain cell types able to uncap the protein. Virus infection characteristics could also be modulated by painting virions with proteins that modulate envelope distribution (e.g. parching). Such modifications of viral envelopes are commonly used to alter the viral tropism.

The viral painting process according to the present invention simplifies the procedure for the generation of such viruses and facilitates the use of various combinations of these approaches to modify infection specificities of viruses and virus derived vector systems.

For example patent application WO2005118802 describes retroviral vectors, particularly lentiviral vectors, pseudotyped with a genetically modified Sindbis virus envelope and targeted to specific cell types via a ZZ domain of protein A linked to the envelope.

Recent publications have demonstrated that for retroviral vectors, target binding and fusion function of envelope proteins may be separated by introducing binding independent fusogenes of e.g. Sindbis virus (Yang L (2006, 2008), Yang H (2008), Ziegler (2008)).

Binding specifities can be provided in a second step i.e. by painting according to the present invention thus providing a high degree of flexibility (a basic vector carrying the fusogene may be equipped with a broad range of different binding molecules)

Another possibility to post-modify viral envelope proteins of virions already released from its host cell is to alter the viral envelope proteins chemically or biochemically.

For example in WO93/09221, influenza virus tropism was modified by inhibition of the viral hemagglutinin polypeptide which normally mediates the binding of the virus to the cellular receptor by means of a monoclonal antibody and by coupling the virus with an antibody capable of interacting with the transferrin receptor expressed onto targeted cells.

Roux et al. (1989, Proc. Natl. Acad Sci. USA 86, 9079-9083) reported the infection of human cells with a mouse ecotropic recombinant retrovirus using two biotinylated antibodies directed to the retroviral envelope gp70 and to a cellular antigen of the human major histocompatibility complex (MHC), respectively.

Such modifications to the viral envelope might additionally be introduced into the viral particle either prior to, subsequent to or simultaneously with the painting procedure of the present invention.

An "enveloped virus" is a virus which exhibits a viral envelope. A viral envelope typically has a protein to lipid mole fraction expressed in mole percentage (mol %) between 50 and 90, preferably 65 to 85 and most preferably 70 to 80. The term "enveloped virus" according to the present invention comprise following taxonomic families, which can be divided in corresponding subfamilies, genus and species, whereas only not limiting representative examples of species are shown. An "enveloped virus" can be selected from any group of family, subfamily, genus or species.

The classification is in accordance with the "VIIIth Report of the International Committee on Taxonomy of Viruses, 2005" (C. M. Fauquet, M. A. Mayo, J. Maniloff, U. Desselberger, and L. A. Ball (eds), Virus Taxonomy, Academic Press, 1162 pp. (2005)) which is herein incorporated by reference. Preferably the "enveloped virus" is a poxvirus, a herpesvirus or a retrovirus, more preferably a gamma retrovirus or a lentivirus, most preferably mouse leukemia virus (MLV) and/or Feline Herpesvirus-1 (FHV-1).

| Family Subfamily | Genus | Species |
|---|---|---|
| Arenaviridae | *Arenavirus* | *Lymphocytic choriomeningitis virus* |
| | | *Lassavirus* |
| Bunyaviridae | *Orthobunyavirus* | *Bunyamwera virus* |
| | *Hantavirus* | *Hantaan virus* |
| | *Nairovirus* | *Dugbe virus* |
| | | *Krim-Kongo virus* |
| | *Phlebovirus* | *Rift Valley fever virus* |
| Coronaviridae | *Coronavirus* | *Infectious bronchitis virus* |
| | *Torovirus* | *Equine torovirus* |
| Filoviridae | *Marburgvirus* | *Lake Victoria marburgvirus* |
| | *Ebolavirus* | *Zaire ebolavirus* |

-continued

| Family Subfamily | Genus | Species |
|---|---|---|
| Flaviviridae | Flavivirus | Yellow fever virus |
| | Pestivirus | Bovine viral diarrhea virus 1 |
| | Hepacivirus | Hepatitis C virus |
| Hepadnaviridae | Orthohepadnavirus | Hepatitis-B-Virus |
| | Avihepdnavirus | Duck Hepatitis-B-Virus |
| Herpesviridae | | |
| | Ictalurivirus | Ictalurid herpesvirus 1 |
| Alphaherpesvirinae | | |
| | Simplexvirus | Human herpesvirus 1 |
| | Varicellovirus | Human herpesvirus 3 |
| | Mardivirus | Gallid herpesvirus 2 |
| | Iltovirus | Gallid herpesvirus 1 |
| Betaherpesvirinae | | |
| | Cytomegalovirus | Human herpesvirus 5 |
| | Muromegalovirus | Murid herpesvirus 1 |
| | Roseolovirus | Human herpesvirus 6 |
| Gammaherpesvirinae | | |
| | Lymphocryptovirus | Human herpesvirus 4 |
| | Rhadinovirus | Saimiriine herpesvirus 2 |
| Orthomyxoviridae | | |
| | Influenzavirus A | Influenza A virus |
| | Influenzavirus C | Influenza C virus |
| | Thogotovirus | Thogoto virus |
| | Influenzavirus B | Influenza B virus |
| | Isavirus | Infectious salmon anemia virus |
| Paramyxoviridae | | |
| Paramyxovirinae | | |
| | Respirovirus | Sendai virus |
| | Morbillivirus | Measles virus |
| | Rubulavirus | Mumps virus |
| | Henipavirus | Hendra virus |
| | Avulavirus | Newcastle disease virus |
| Pneumovirinae | | |
| | Pneumovirus | Human respiratory syncytial virus |
| | Metapneumovirus | Avian metapneumovirus |
| Poxviridae | | |
| Chordopoxvirinae | | |
| | Orthopoxvirus | Vaccinia virus |
| | Parapoxvirus | Orf virus |
| | Avipoxvirus | Fowlpox virus |
| | Capripoxvirus | Sheeppox virus |
| | Leporipoxvirus | Myxoma virus |
| | Suipoxvirus | Swinepox virus |
| | Molluscipoxvirus | Molluscum contagiosum virus |
| | Yatapoxvirus | Yaba monkey tumor virus |
| Entomopoxvirinae | | |
| | Alphaentomopoxvirus | Melolontha melolontha entomopoxvirus |
| | Betaentomopoxvirus | Amsacta moorei entomopoxvirus 'L' |
| | Gammaentomopoxvirus | Chironomus luridus entomopoxvirus |
| Retroviridae | | |
| Orthoretrovirinae | | |
| | Betaretrovirus | Mouse mammary tumour virus |
| | | Jaagsiekte sheep retrovirus |
| | | Langur virus |
| | | Mason-Pfizer monkey virus |
| | | Squirrel monkey retrovirus |
| | Gammaretrovirus | Murine leukemia virus |
| | | Feline leukemia virus |
| | | Gibbon ape leukemia virus |
| | | Guinea pig type-C oncovirus |
| | | Porcine type-C oncovirus |
| | | Finkel-Biskis-Jinkins murine sarcoma virus |
| | | Gardner-Arnstein feline sarcoma virus |
| | | Hardy-Zuckerman feline sarcoma virus |
| | | Harvey murine sarcoma virus |
| | | Kirsten murine sarcoma virus |
| | | Moloney murine sarcoma virus |
| | | Snyder-Theilen feline sarcoma virus |
| | | Woolly monkey sarcoma virus |
| | | Viper retrovirus |
| | | Chick syncytial virus |
| | | Reticuloendotheliosis virus |
| | | Trager duck spleen necrosis virus |
| | Alpharetrovirus | Avian leukosis virus |
| | | Rous sarcoma virus (RSV) |
| | | Avian myeloblastosis virus |
| | | Avian carcinoma Mill Hill virus |

-continued

| Family | Subfamily | Genus | Species |
|---|---|---|---|
| | | | Avian myelocytomatosis virus 29 |
| | | | Avian sarcoma virus CT10 |
| | | | Fujinami sarcoma virus |
| | | Deltaretrovirus | Bovine leukemia virus |
| | | | Human T-cell lymphotropic virus type I |
| | | | Human T-cell lymphotropic virus type II |
| | | | Simian T-cell lymphotropic virus type I |
| | | | Simian T-cell lymphotropic virus type II |
| | | Lentivirus | Human immunodeficiency virus 1 |
| | | | Human immunodeficiency virus 2 |
| | | | Simian immunodeficiency virus (SIV) |
| | | | Bovine immunodeficiency virus (BIV) |
| | | | Jembrana Disease Virus |
| | | | Equine infectious anemia virus (EIAV) |
| | | | Feline immunodeficiency virus (FIV) |
| | | | Maedi visna virus (MVV) |
| | | | Caprine arthritis encephalitis virus |
| | | Epsilonretrovirus | Walleye dermal sarcoma virus |
| | | | Walleye epidermal hyperplasia virus 1 |
| | | | Walleye epidermal hyperplasia virus 2 |
| | Spumaretrovirinae | | |
| | | Spumavirus | Simian foamy virus |
| | | | Feline foamy virus |
| | | | Equine foamy virus |
| | | | Bovine foamy virus |
| Rhabdoviridae | | | |
| | | Vesiculovirus | Vesicular stomatitis Indiana virus |
| | | Lyssavirus | Rabies virus |
| | | Ephemerovirus | Bovine ephemeral fever virus |
| | | Novirhabdovirus | Infectious hematopoietic necrosis virus |
| Togaviridae | | | |
| | | Alphavirus | Sindbis virus |
| | | Rubivirus | Rubella virus |

"Exogenous" in the context of the present invention means that the compounds to be inserted into the virus envelope are added to isolated enveloped viruses in an appropriate suspension medium like body fluid, buffered saline or cell culture medium e.g. DMEM. The presence of a cellular host is not necessary. The method is termed "viral painting".

The terms "altered" or "modified" viral particle, virion or virus in the context of the present invention are used interchangeably. All terms refer to enveloped viruses wherein the composition of the viral envelope is modified by anchoring of compounds into the lipid double layer of the virus envelope after release (post release) of the viral particle from its respective host cell, preferably after isolation and concentration of intact viral particles from its natural environment or a technical production process. The modification of the composition of the virus envelope can be used to modify the chemical and/or biological characteristics of a virus particle. For example the stability of viruses against sheering forces or the resistance to detergents can be adjusted. Also important is the possibility to modify the infectivity, affinity or the host spectrum of the virions, allowing for a specific design of therapeutic viral vectors e.g. with pre-designed tissue specificity or vaccines that preferentially infect professional antigen presenting cells. Anchoring of protein marker and/or compounds having moieties with specific chemical or physical properties can be used to enhance the detectability and/or sensitivity of diagnostic methods. Linkage of molecules with immunological functions, most notably cytokines, by the viral painting process can provide a range of novel properties to the virion e.g. stimulation of the immune system. Painted enveloped viral vectors can be turned into specific adjuvants for vaccination approaches through an increased immunogenicity. The flexibility and the speed of the modular viral painting will be especially useful for vaccination approaches against viruses that frequently change or rearrange their antigens (e.g. influenza) or are difficult to target (e.g. HIV-I). Cytokines are a category of signaling molecules that, like hormones and neurotransmitters, are used extensively in cellular communication. They are proteins, peptides or glycoproteins.

The term "cytokine" encompasses a large and diverse family of polypeptide regulators that are produced widely throughout the body by cells of diverse embryological origin.

Cytokines may be divided into six groups: interleukins, colony-stimulating factors, interferons, tumor necrosis factor, growth factors, and chemokines.

Interleukins are proteins that are produced mainly by lymphocytes or macrophages and act on other leukocytes. At least 18 types with varying origin and function exist.

Colony-stimulating factors are produced by lymphoid and nonlymphoid cells. These factors provide a mechanism whereby cells that are distant from bone marrow can call for different types of hemopoietic progeny. There are also growth-promoting actions of locally produced colony-stimulating factors within the bone marrow to stimulate progenitors to differentiate into macrophages, granulocytes, or colonies containing both cell types.

Interferons classically interfere with the virus replication mechanisms in cells. Interferon-β (produced by leukocytes) and interferon-γ (produced by fibroblasts) activate cytotoxicity in natural killer cells. Interferon-γ also activates natural killer cells, and is a potent activator of macrophages as well.

Tumor necrosis factor-α (TNF-α is produced by a variety of cell types, but activated macrophages represent the dominant source. TNF-α activates natural killer cell cytotoxicity, enhances generation of cytotoxic T-lymphocytes, and activates natural killer cells to produce interferon-β. TNF-α also acts on vascular endothelium to promote inflammation and thrombosis. TNF-α may also induce apoptosis in cells such as trophoblasts. TNF-β is a product of Th1 T-cells; in addition to providing help in proinflammatory cell-mediated immune responses, these cells produce delayed-type hypersensitivity reactions where macrophages are locally recruited and activated to kill intracellular pathogens, such as certain bacteria. TNF-β has interferon-type activity and a narrower spectrum of action than TNF-α.

Transforming growth factors (TGFs) have the ability to promote unrestrained proliferation of cells which otherwise has a benign behavior phenotype. These factors have therefore been implicated in development of cancer. There are two groups of transforming growth factors. TGF-α is a 5-kilodalton peptide produced by a variety of cells and collaborates with TGF-β a 25-kD peptide, in promoting unrestrained tumorlike growth. TGF-β has potent pleiotropic effects on a wide variety of tissues and is a potent fibrogenic and immunosuppressive agent.

Chemokines are chemoattractant cytokines of small (7-14 kD) heparin-binding proteins that are subdivided into four families: CXC, CC, C, and CX3C. Chemokines are produced by macrophages stimulated by bacterial endotoxins, and control the nature and magnitude of cell infiltration in inflammation. Preferred cytokines according to the present invention are interleukins and colony-stimulating factors, especially interleukin-1 (IL-2), interleukin-4 (IL-4), granulocyte-macrophage colony stimulating factor (GM-CSF) and/or Interleukin-12 (IL-12), preferably of human origin.

For painting purposes according to the present invention fusion proteins consisting of cytokines and membrane anchor domains are used. The cytokines are preferably fused at their C-terminus to a membrane anchor domain which preferably is GPI. The C-terminal stop codon of the cytokine is hereby replaced by a short linker sequence e.g. polyglycine.

A "compound" according to the present invention is a chemical substance which is capable of inserting or integrating itself into lipid double layers, especially of viral envelopes. Such compounds consist of at least two distinct parts: (a) a membrane anchor domain or moiety and, (b) a hydrophilic target domain or moiety to be exposed to the outside of the viral particle. Such compounds may contain further parts, providing for additional physical or chemical properties or to allow for linkage to other materials such as nanoparticles or beads. Compounds may contain also protein-tags such as the histidine tag and/or flag-tag, that is important for purification of said compounds or for purification and/or concentration of viral particles modified with said compounds.

Membrane anchor domains" are amphiphilic molecules which are able to integrate into lipid double layers with their lipophilic part, whereas the hydrophilic part is exposed to the surrounding watery medium. The hydrophobic group is typically a large hydrocarbon moiety, such as a long chain of the form R=CH3(CH2)n, with n>4 or a cyclic hydrocarbon moiety. The hydrophilic group can either be charged or polar, uncharged groups. Charged groups are e.g. carboxylates: RCO2-; sulfates: RSO4-; sulfonates: RSO3-. phosphates (the typical charged functionality in phospholipids), carbohydrates or amines RNH3+. Polar, uncharged groups are alcohols with large R groups, such as diacyl glycerol (DAG), and oligoethyleneglycols with long alkyl chains. Some amphiphilic membrane anchor domains like GPI have several hydrophobic parts, several hydrophilic parts, or several of both.

Preferred membrane anchor domains are phospholipid-polyethylenglycol, stearyl, cholesterol, chelator lipid, nitrilotriacetic acid ditetradecylamine (NTA-DTDA), farnesyl or palmitoyl moieties. Most preferred is Glycosylphosphatidylinositol (GPI).

"Target domains or target moieties" according to the present invention are covalently joined to the hydrophilic part of membrane anchor domains. Target domains are preferably proteins or polypeptides, herein also named target proteins e.g. enzymes, antigen recognition sides, receptors, protein markers, fluorescence markers or proteins, or peptide hormones or cytokines. Such target domains could be further modified by joining of protein tags and/or other functional groups (e.g. biotinyl residues, cross linkers, carbohydrates). A preferred target protein is enhanced green fluorescent protein (EGFP) or red fluorescent protein and their variants, especially monomeric forms (Zaccharias (2002), Campbell (2002)). CD59 or CD55 are preferred as compounds naturally consisting of a membrane anchor domain and a target protein. CD59 or CD55 can be used to protect viral particles against the complement system of an animal, preferably a human host. Non-proteinic target domains could be e.g. polysaccharides, nucleic acids, dyes, radioactive ligands, or fluorescent dyes. Even more complex structures like polystyrol beads or (nano) magnetic particles could be joined to a membrane anchor domain.

The term "protein tag" refers to peptide sequences genetically grafted onto a recombinant protein. Often these tags are removable by chemical agents or by enzymatic means, such as proteolysis or intein splicing. Tags can be attached to proteins for various purposes:

Affinity tags are appended to proteins so that they can be purified from their crude biological source using an affinity technique. These include chitin binding protein (CBP), maltose binding protein (MBP), and glutathione-s-transferase (GST). The poly(His) tag is the most widely-used protein tag and it binds to metal matrices. Some affinity tags have a dual role as a solubilisation agent, such as MBP and GST.

Chromatography tags are used to alter chromatographic properties of the protein to afford different resolution across a particular separation technique. Often, these consist of polyanionic amino acids, such as FLAG tag.

Epitope tags are short peptide sequences which are chosen because high-affinity antibodies can be reliably produced in many different species. These are usually derived from viral genes and include e.g. V5-tag, c-myc-tag, and HA-tag. These tags are particularly useful for western blotting and immuno precipitation experiments, although they also find use in antibody purification.

Fluorescence tags are used to give visual readout on a protein. EGFP and its variants are the most commonly used fluorescence tags.

Protein tags find many other usages, such as specific enzymatic modification (such as biotin ligase tags) and chemical modification (FLaSH) tag.

Tags can also be combined to produce multifunctional modifications of the protein.

Tethering of target proteins to lipid membranes is achieved in several different ways, most simply by stretches of hydrophobic amino acids forming trans-membrane domains which can be joined to proteins of interest. A more complex way to associate proteins to membranes is via post-translational modification of proteins with lipophilic residues e.g. farnesyl or palmitoyl moieties. Modification of proteins with glycosylphosphatidylinositol (GPI) anchors probably constitutes the most complex way of attaching proteins to lipid membranes.

Figure 3:
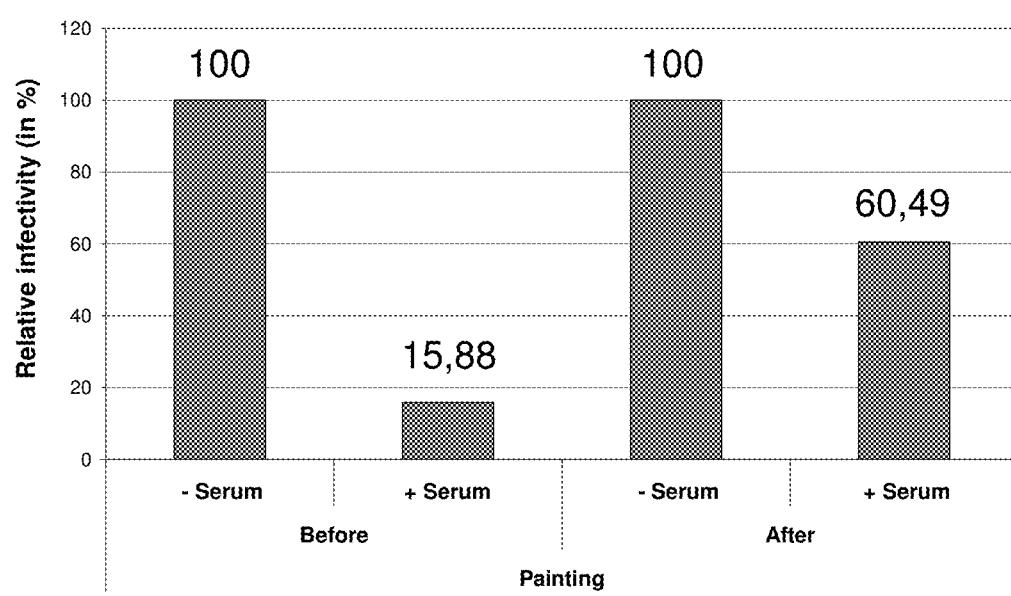

"Glycosylphosphatidylinositol" (GPI anchor) (FIG. 3) is a glycolipid that can be attached to the C-terminus of a protein during posttranslational modification within a cell or chemically. It is composed of a hydrophobic phosphatidyl inositol group linked through a carbohydrate containing linker (glucosamine and mannose glycosidically bound to the inositol residue) to the C-terminal amino acid of a mature protein. The two fatty acids within the hydrophobic phosphatidyl inositol group anchor the protein to the cell membrane.

Glypiated proteins contain a signal peptide, thus directing them with translation into the endoplasmic reticulum (ER). The C-terminus is composed of hydrophobic amino acids which stay inserted in the ER membrane. The hydrophobic end is then cleaved off and replaced by the GPI-anchor. As the protein processes through the secretory pathway, it is transferred via vesicles to the Golgi apparatus and finally to the extra cellular space where it remains attached to the exterior leaflet of the cell membrane. Since the glypiation is the sole means of attachment of such proteins to the membrane, cleavage of the group by phospholipases will result in controlled release of the protein from the membrane.

Proteins targeted for GPI anchoring contain a GPI signalling sequence (GSS) at the C-terminal end in addition to the signal peptide sequence (SP) located at the N-terminus necessary for translocation of nascent proteins into the endo plasmatic reticulum (ER). The GSS contains a hydrophilic spacer sequence of 8-12 amino acids followed by a hydrophobic region of between 8 and 20 amino acids and the site of GPI attachment is restricted to a protein specific 6 amino acids motif. Additionally, it has been shown that protein folding is not required for GPI anchor addition and hence that the size or sequence of the protein does not have an effect on the addition of GPI. The GSS is recognized in the ER by the transamidase enzyme complex which consists of at least 5 subunits all of which are required for correct function and is replaced by the preformed GPI anchor. The biochemical pathway for synthesis of the GPI anchors is complex and chemical structures of GPI anchors vary to a great degree, however a common backbone structure is observed: Linkage of the GPI anchor to the C-terminal end of the protein is achieved by an amide bond to phosphoethanolamine. The following central three mannose residues are linked via a non-acetylated glucosamine to the phosphoinositol part, which in turn is associated to the lipid residues, usually acyl or aryl fatty acid chains or sphingolipids e.g. ceramide.

A "fusion protein" according to the present invention can be produced by methods already known in the art. These methods include, for example, in vitro recombinant DNA techniques, chemical techniques and in vivo recombination/genetic recombination. DNA and RNA synthesis may, additionally, be performed using an automated synthesizer as described e.g. in Sambrook et al., (Sambrook, J, Fritsch, E F & Maniatis, T; H Eds. (1989). Molecular Cloning—A Laboratory Manual, 2nd Edition. Cold Spring Habour Laboratory Press).

The preparation of such a fusion protein generally entails the preparation of a first and second or even more DNA coding region and the functional ligation/joining of such regions, in frame, to prepare a single coding region that encodes the desired fusion protein.

The preparation of such a fusion protein generally entails the preparation of a first and second or even more DNA coding region and the functional ligation/joining of such regions, in frame, to prepare a single coding region that encodes the desired fusion protein.

In a preferred embodiment, a DNA sequence coding for the target protein is e.g. joined in frame with a DNA sequence encoding for a protein tag (TAG). The ligation can be designed for the N-terminal region or for the C-terminal region of the target protein. Depending on the proteins used, it might be necessary to introduce a peptide spacer for linkage of the two parts of the fusion protein. These peptide spacers could be either cleavable or non-cleavable. The DNA sequence of the fusion protein or of the target protein alone is then ligated to a signal peptide sequence at the C-terminus and a DNA sequence preferably of a GPI anchoring signal sequence (GSS) is ligated to the N-terminus.

| C-terminus | SP - TAG - Target protein - GSS | N-terminus |
|---|---|---|
| C-terminus | SP - Target protein - TAG - GSS | N-terminus |
| C-terminus | SP - Target protein - GSS | N-terminus |

SP: Signal Peptide;
TAG: Protein Tag;
GSS: GPI anchoring signal sequence

Alternatively, cross-linking reagents could be used to form molecular bridges that chemically tie together functional groups of two different molecules, especially to join an isolated membrane anchor domain, preferably a GPI to the respective target domain.

Generally, hetero-bifunctional cross-linkers are preferred to eliminate unwanted homopolymer formation. Heterobifunctional cross-linkers contain two reactive groups: one generally reacting with primary amine group (e.g., N-hydroxy succinimide (NHS)) and the other generally reacting with a thiol group (e.g., pyridyl disulfide, maleimides, halogens, etc.). Through the primary amine reactive group, the cross-linker may react with the lysine residue(s) of one protein and through the thiol reactive group, the cross-linker, already tied up to the first protein, reacts with the cysteine residue (free sulfhydryl group) of the other protein.

Therefore, polypeptides or proteins generally have, or are derivatised to have, a functional group available for cross-linking purposes. This requirement is not considered to be limiting in that a wide variety of groups can be used in this manner. For example, primary or secondary amine groups, hydrazide or hydrazine groups, carboxyl, alcohol, phosphate, or alkylating groups may be used for reaction with cross-linking reagents.

The spacer arm between the two reactive groups of cross-linkers may have various length and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents). The use of peptide spacers, such as L-Leu-L-Ala-L-Leu-L-Ala, is also contemplated.

It is preferred that a cross-linker having reasonable stability in blood or other body fluids will be employed. Numerous types of disulfide-bond containing linkers are known that can be successfully employed. Exemplary hetero-bifunctional cross-linkers are SMPT, SPDP, LC-SPDP, Sulfo-LC-SPDP, SMCC, Sulfo-SMCC, MBS, Sulfo-MBS, SIAB, Sulfo-SIAB, SMPB, Sulfo-SMPB, EDC/Sulfo-NHS or ABH. Linkers that contain a disulfide bond that is sterically hindered may prove to give greater stability in vivo, preventing release of the agent prior to binding at the site of action. These linkers are thus one preferred group of linking agents.

One of the further preferred cross-linking reagents used is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached viral particle to its target site e.g. a specific tissue or tumour.

Figure 2B:
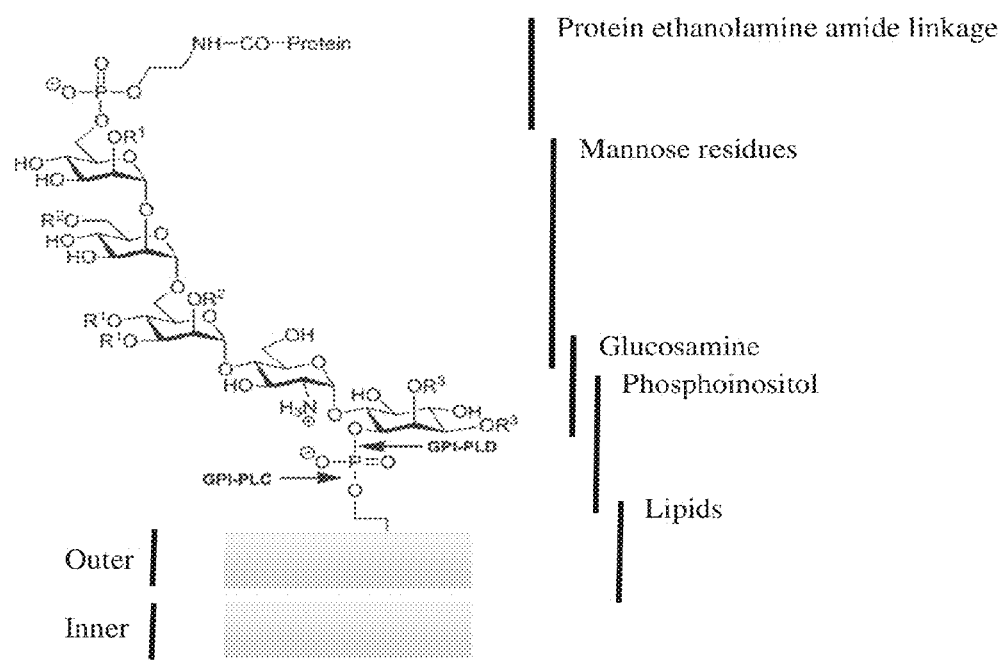

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers can also be employed in accordance herewith. Other useful cross-linkers, not considered to contain or generate a protected disulfide, include SATA, SPDP and 2-iminothiolane. The use of such cross-linkers is well understood in the art.

Once conjugated, the conjugate is separated from unconjugated components and from other contaminants. A large number of purification techniques are available for use. Purification methods based upon size separation, such as gel filtration, gel permeation or high performance liquid chromatography will generally be of most use. Other chromatographic techniques, such as Blue-Sepharose separation, may also be used.

A "pharmaceutical composition" according to the present invention may include beside a therapeutically effective amount of the surface modified viral particle, in general, one or more pharmaceutical acceptable and/or pharmacologically acceptable carriers, additives, antibiotics, preservatives, adjuvants, diluents and/or stabilizers.

The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. Further such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like. The use of such media and agents for pharmaceutical active substances is well known in the art. For human administration, preparations should meet sterility, pyrogenicity, general safety and purity standards as required by FDA Office of Biologics standards or according to the EudraLex rules governing medicinal products in the European Union.

In the present invention also procedures for modifying lipid envelopes of enveloped viruses, preferably of retroviral and lentiviral vectors (RV, LV) or herpesviral vectors with compounds which could be selected from a group containing GPI protein conjugates or proteins conjugated to lipophilic moieties like ppescfpmcphospholipid-polyethyleneglycol, stearyl, cholesterol, farnesyl, palmitoyl, myristoyl, chelator lipid or nitrilotriacetic acid ditetradecylamine (NTA-DTDA) are described. Most preferably GPI protein conjugates are used. The virus remains infectious after these procedures. However, if desirable the viral vectors could also be inactivated prior to or subsequent to the viral painting process, e.g. for vaccination purposes. Techniques are commonly known in the art.

Potential applications include novel targeting strategies for gene therapy, immune modulation (Kueng (2007); Skountzou (2007)) (e.g. enhancement of vaccine efficacy by immune stimulation, protection of retroviral gene therapy vectors by immune inhibition) or to implement pharmacogenetics in retroviral gene therapy by quick adaptation to different therapy requirements in patient sub-groups. In addition to potential clinical uses, virus painting provides a quick way to specifically tag and modify viral envelopes e.g. for fluorescence imaging, affinity purification, labeling to magnetic particles (see later discussions) and radio labeling.

As model compounds CD59 (protectin, MACIF, SwissProt accession number P 13987) and EGFP linked to GPI were used. CD59 has widely been studied and was also shown to confer partial resistance against human complement to modified murine leukemia virus (MLV) particles (Breun (1999)). To facilitate purification and analysis of CD59, a protein tag consisting of six consecutive histidine residues were introduced directly at the N-terminus of the mature protein. These histidine tags are also potentially useful in downstream applications: After painting of virions with CD59his they can be associated via the histidine tags with e.g. magnetic nanoparticles to allow for easy purification and concentration of virions. In addition magnetic virus could be targeted by magnetic fields or used for magneto thermic therapy (Chan (2005); Ito (2005)), thus creating a new link between protein engineering and nanobiotechnology. First studies demonstrated the usefulness of magnetic particles in anti-tumor strategies (Jordan (2006), Wilhelm (2007)).

The results (see FIG. 2) show that exogenously added recombinant CD59his associates with concentrated retroviral and lentiviral particles. Data from immunoblotting suggest that the efficacy of the process allows for the association of between 1 and 5% of the total amount of CD59his (compare FIG. 1B, 5% and 10% lanes respectively with corresponding VP+ lanes) leading to estimates of between 5 and 250 molecules per virion which is sufficient to elicit biologically relevant effects. Depending on the concentration of target compounds used during the incubation step the amount of target domains incorporated into the envelope of the painted virus can be adjusted. It seems that there is a reciprocal correlation between the number of target domains anchored in the viral envelope and the infectivity of the virus i.e sterical hindrance of excessive protein moieties will reduce access of the env molecules to the cognate receptors. Sufficient results were obtained with a load of 10 to 150 molecules per virion, preferably 10 to 50 molecules per virion. Generally the infectivity was slightly reduced when compared to infection levels before painting. This could be due to a steric hindrance of the natural viral envelope proteins. However, when comparing infection levels for GPI-associated virions to non-associated virus particles only a small difference is observed (FIG. 2, compare lanes VP− and VP+). This indicates that the duration of the process (5 to 6 hours in total) rather than the painting process itself is responsible for the decrease in infectivity. Using shorter incubation times for painting and alternative purification post-painting procedures e.g. ultrafiltration or magnetic purification decrease handling times leads to higher infection rates.

As the vast majority of proteins can be removed by post-painting procedures like e.g. ultracentrifugation, the incorporation process appears to be specific. The control protein (rat IgG) is a soluble protein of hydrophilic character with consequentially low affinity for hydrophobic surfaces. The possibility remains that proteins with substantial hydrophobic sequence motifs, e.g. trans-membrane proteins, could show comparable behaviour to GPI proteins, somehow similar to the formation of proteoliposomes. Virions remained infectious after painting and post-painting treatments (FIG. 2). Another advantage of using GPI anchors for modification of proteins is that the amino acid sequence of the mature protein is not altered increasing the possibility for functionally intact proteins. Addition of the hydrophobic moiety might however influence folding of the recombinant GPI protein thereby destroying conformational epitopes or the active centers of enzymes. Moreover, preliminary experiments suggested that levels of painting are increasing with increases of virus numbers and GPI protein amount. This indicates that the amount of GPI proteins after painting on virions is controllable. There are a number of potential uses for this technique: Addition of immune-stimulatory GPI-linked factors could enhance the efficacy of vaccination (Skountzou (2007)) or provide an important added benefit for viral suicide gene therapy. Immune inhibitory molecules might help to protect viral gene transfer vectors from unwanted or premature immune responses. The inherent flexibility of a modular system (i.e. adding different types of GPI-linked molecules to viruses directly prior to use) would allow for quick and adaptive responses to therapy needs for example in response to genetic heterogeneity in patients.

Virus painting can also be used to attenuate existing or new vaccines to enhance safety by either (i) reducing virulence or the efficiency of the infection event (ii) targeting the virus so that it preferentially infects cells that do not allow productive infection or (iii) retargeting to professional antigen presenting cells e.g. targeting to C-type lectin receptors is known to induce potent helper and cytolytic T-cell responses (Keler (2007)) or e.g. using a chimeric ErbB2 linked to CTLA-4 B7 interacting domain (Rohrbach (2005)). Viral painting also allows for the direct labeling of viral envelope membranes, thus facilitating concentration, purification and/or visualization of virions e.g. for diagnostic purposes. Incorporation of specific chemical moieties into viral envelops are also useful for lowering of detection limits in common qualitative and quantitative immunoassays, such as ELISA or for PCR and/or FACS analysis. The methods presented herein are especially useful as part of a diagnostics system or diagnostic kit. Furthermore they can be used for isolation, detection, or measurement of known or unknown enveloped virus.

GPI tagging allows for specific concentration of known or unknown enveloped virus in any given sample, preferably in body fluid, cell culture medium or buffered saline. Therefore, new applications for virus purification and/or concentration and/or isolation are presented. This tool may conceivably developed as a major component of a new diagnostics system to quickly and easily purify and identify and/or quantify known or unknown viruses from biological samples, research samples or clinical samples. Currently, classic ultra-centrifugation techniques or more modern ultra-filtration methods using regenerated cellulose, poly ether sulphone or cellulose triacetate commercially available membranes from Sartorius (Vivaspin) or Millipore (Centricon) are used to non-specifically collect or concentrate viruses from samples. These methods are however non-specific, i.e. all viruses and everything having the same size as viruses will also be collected e.g. serum protein complexes from cell culture media. This can lead to many diverse problems with downstream protocols due to such contaminations. Also ultra-filtration only works in certain settings due to problems with non-specific sticking of virus with the membranes. Hence a specific way to tag enveloped viruses from a sample via compounds, preferably recombinant GPI proteins with histidine tags and magnetic nanoparticles would be a novel and improved way to achieve purification for further downstream identification methods such as ELISA, or PCR based assays. FIG. 1 shows that the GPI protein associates to retroviral and lentiviral vectors and FIG. 5 shows exemplarily association with other enveloped virus types, in this case feline herpes virus. FIG. 6 shows that 2 model recombinant GPI proteins (namely CD59 and GFP) can both be highly efficiently attached to and manipulated by magnetic force by virus-sized magnetic nanoparticles (MNP). This clearly shows that both necessary components of the proposed system are functional, i.e. GPI-virus and GPI-MNP interactions. An additional benefit is that infection based assays, e.g. focus forming unit or plaque assays can also be adopted as the GPI tagging process does not affect the virus infectivity in contrast to the more conventional methods described above. For completeness, it must also be mentioned that affinity techniques, mostly based on column format using anti-viral envelope protein antibodies, is also an option for specifically isolating viruses, however, this is limited to a situation where the virus is known, it is expensive and also leads to the purification of a non-infectious virus and is therefore also not viable alternative to the applications suggested above for newly proposed GPI tagging tool.

We have also successfully demonstrated that the methods also work with other enveloped viruses such as influenza virus, pox virus, HBV and herpes virus, for an example see feline herpes virus (FIG. 5). The protein tags were engineered into CD59his initially for the purpose of easy purification. However, the tags can also be used for the linkage of magnetic micro- or nanoparticles to the CD59his and subsequently to the virion, thus creating a link between retrovirology and nanotechnology. Magnetic retrovirus could be easily concentrated and purified via exposure to magnetic fields (Chan (2005)). In addition magnetic fields could be used in targeting particles and inducing hyperthermia (Ito (2005); Jordan (2006); Wilhelm (2007)). Taken together, the direct transfer of GPI-linked his-tagged proteins onto enveloped viral particles is a potentially valuable tool for a variety of both research and clinical applications.

SUMMARY OF THE INVENTION

A method for exogenously modifying the envelope composition of an enveloped viral particle, comprising the steps (a) Concentration of isolated viral particles from a suspension fluid (b) Incubation of the concentrated viral particles with a reactant consisting of a hydrophilic target domain or moiety covalently linked to a lipophilic membrane anchor domain or moiety, wherein the lipophilic membrane anchor domain becomes integrated into the lipid double layer of the virus envelope and wherein the hydrophilic target domain becomes exposed to the surrounding watery incubation fluid (c) Separation of envelope modified viral particles from excessive reactants A method comprising the steps (a) Incubation of a fluid containing enveloped viral particle with a reactant consisting of a hydrophilic target domain or moiety covalently linked to a lipophilic membrane anchor domain or moiety, wherein the lipophilic membrane anchor domain becomes integrated into the lipid double layer of the virus envelope and wherein the hydrophilic target domain or moiety becomes exposed to the surrounding fluid (b) Separation of envelope modified viral particles from excessive reactants (c) Detection of the envelope modified viral particles.

Methods as described above, wherein the total protein content of the viral envelope in relation to the total lipid content of the viral envelope is between 50:50 and 90:10, preferably 65:35 to 85:15 and most preferably 70:30 to 80:20 mol %

A method as above wherein the lipophilic membrane anchor domain is selected from the group comprising phospholipid-polyethyleneglycol, stearyl, myristyl, cholesterol, chelator lipid nitrilotriacetic acid ditetradecylamine (NTA-DTDA) and glycosylphosphatidylinositol (GPI) or analogues thereof, whereas analogues of GPI anchor domains are mimics wherein portions of the glycan core are systematically replaced with unnatural linkers of comparable length and dimension. Those analogues might contain no, one or two mannose units and replace the phosphoinositol and glucosamine units with a simple hydrophilic poly(ethylene glycol) linker which allows for the installation of various side chains and different lipid tails A method as above wherein the hydrophilic target domain is selected from the group comprising polysaccharides, nucleic acids, dyes, radioactive ligands, fluorescent dyes, synthetic beads or magnetic particles, wherein the synthetic beads or the magnetic particles can be coated or uncoated. A method as above, wherein the hydrophilic target domain is a protein or a polypeptide.

A method as above, wherein the protein or the polypeptide further contains a protein tag or combinations of protein tags.

A method as above, wherein the protein or the polypeptide is an enzyme, an antibody, a receptor, a marker protein, a fluorescence protein, a complement inhibitor or a cytokine. A method as above wherein the complement inhibitor is CD59 or CD55 and the cytokine is a interleukin and/or colony-stimulating factor, preferably IL-2, IL-4 or IL-12

A method as above, wherein the hydrophilic target domain and the lipophilic membrane anchor domain are chemically joined by a cross linker.

A method as above, wherein one or more different reactants are used or combined.

A method as above, wherein the suspension fluid is a body fluid, a cell culture medium, a physiological saline or a buffered saline A method as above, wherein the concentration of isolated viral particles and/or separation of envelope modified viral particles is achieved by ultracentrifugation, ultrafiltration or chromatography, especially affinity chromatography A method as above, wherein the incubation step is achieved by slow agitation in body fluid, cell culture medium, buffered saline or physiological saline at temperatures between 4 to 40° C. for incubation times between 10 min and 48 hours A method as above, wherein the temperature is preferably between 25 and 38° C. and/or the incubation time is between 1 and 3 hours.

A method as above, wherein the enveloped viral particle is selected from the group comprising Arenaviridae, Bunyaviridae, Coronaviridae, Filoviridae, Flaviviridae, Hepadnaviridae, Herpesviridae, Orthomyxoviridae, Paramyxoviridae, Poxviridae, Retroviridae, Rhabdoviridae and Togaviridae A method as above, wherein the viral particle is a retrovirus, especially mouse leukemia virus or a lentivirus or a poxvirus, especially small poxvirus or a vaccinia virus preferably MVA or NYVAC or a herpesvirus, especially feline herpes virus.

A method as above, wherein the genome of the viral particle is genetically modified compared to its wild-type form. A method as above, wherein the viral particle is inactivated prior to or subsequent to the painting method.

A method as above, wherein the painting process is carried out prior to, simultaneously with or post to other methods for modifying the viral envelope.

A viral particle produced by a method as above. A pharmaceutical composition containing a therapeutically effective amount of the viral particle as above and a pharmaceutically acceptable carrier Use of the viral particle or of the pharmaceutical composition as above as a medicament Use of the viral particle or of the pharmaceutical composition as above for gene therapy, vaccination, or immunomodulation Use of the viral particle as above for attenuation of vaccines especially to enhance the safety of vaccines by (i) reducing virulence or the efficiency of the infection event (ii) targeting the virus so that it preferentially infects cells that do not allow productive infection and/or (iii) retargeting to professional antigen presenting cells e.g. targeting to C-type lectin receptors.

Use of the method as above for concentration of viral particles as an enrichment tool for research and diagnosis purposes, especially to facilitate said research/diagnostic applications by removal of contaminants (e.g. salts, proteins and protein complexes). A diagnostic method as above, wherein the enveloped viral particles are detected by Immunoassays, chromatography, FACS analysis or microscopy.

Use of the method as above for diagnosis and/or visualization of virus particles.

A kit containing at least the reactant containing a hydrophilic target domain or moiety covalently linked to a lipophilic membrane anchor domain or moiety for use in the methods described above, and instructions for performing the methods as above.

SHORT DESCRIPTION OF THE DRAWINGS

FIG. 1A depicts the painting of retroviral and lentiviral vector particles in a schematic overview. This overview is based on the following experiment: concentrated supernatants from retroviral (RV) or lentiviral (LV) producer cell lines (293gpalfpLXSNeGFP and STAR-A-HV, respectively) are incubated with purified and concentrated CD59his for 3-20 hours at 37° C. under constant shaking. After incubation samples are purified by ultracentrifugation (2 hrs, 20 000 rpm, 4° C.) to remove non-virus-associated proteins. Before analysis of CD59his, endogenous CD59 is removed by using magnetic nickel beads (Promega). Samples were analysed by immunoblotting using antibodies directed specifically against CD59, MLV capsid (CA) and HIV-1 p24. FIG. 1B shows the analysis of painted retrovirus: concentrated supernatants from parental cells (PC) and virus producing cells (VP) were incubated in the presence or absence of CD59his for 21 hours at 37° C. under constant shaking. In addition cell culture medium (ME) was also incubated under the same conditions. After purification as detailed above, cells were analysed by immunoblotting. Results show that CD59his is only retained during purification in the presence of virus and CD59his (RV and LV, upper panels respectively, compare lanes VP− and VP+) indicating association of the protein with viral particles. On the same gels, either 5 or 10% respectively of the amount of CD59his used for viral painting was loaded to assess efficiency of painting. Levels of viral gag proteins are shown via immunoblots using MLV capsid and HIV-1 p24 antibodies. Viral proteins are only present in supernatants derived from viral producers. (RV and LV, lower panels respectively, compare lanes VP− and +). FIG. 1C shows the specificity of viral painting: concentrated viral supernatant were mixed with CD59his and the same amount of a non-GPI protein (rat IgG; MW 150 kD; Dako). The sample was incubated for approximately 20 hours. Aliquots are taken before and after ultracentrifugation and silver-stained to assess protein content. 100% and 10% of the used amount of IgG were loaded for comparison. Ultracentrifugation removes the majority of proteins as well as the IgG contaminant. FIG. 1D shows infectivity after Painting: Virus supernatants post-painting are purified by ultracentrifugation and used to infect target HeLa cells. After 36 hours supernatant is removed and analysed by immunoblotting for presence of CD59his to confirm painting. Cells analysed by flow cytometry. No infection was observed in HeLa cells treated with medium (mock) or supernatant from parental cells that was incubated with CD59his (PC+). Virus supernatant in the absence or presence of CD59his (VP−; VP+) shows infection rates of approximately 4%. Supernatants treated with CD59his performed slightly worse in infection experiments. As infection control viral supernatant saved before painting (one tenth of the volume used for infection after painting) was used (VP). Infectivity was reduced significantly after painting. Error bars represent means+/−standard deviation.

FIG. 2A schematically shows that the-N-terminal signal peptide (SP) of the nascent polypeptide chain leads to translocation to the ER. The transamidase complex located at the ER membrane, recognizes the Glycosylphosphatidylinositol (GPI) anchoring signal sequence (GSS) and replaces it with the preformed GPI anchor. FIG. 2B schematically shows that a common backbone structure is observed in GPI anchors. Linkage to the protein part is achieved by an amide bond to phosphoethanolamine. The following carbohydrate core consists of three mannose and a glucosamine residue. The phosphoinositol group links the hydrophobic lipid part, mainly aryl, acyl or ceramide type lipids, to the remaining GPI anchor. The hydrophobic moieties are inserted into the outer leaflet of the cell membrane. Sites of cleavage for mammalian GPI-specific phospholipases C and D (GPI-PLC and GPI-PLD, respectively) are indicated by arrows.

FIG. 3: Serum protection after viral painting. An experiment (n=1) was carried out to determine serum protection of virions painted with CD59his. After painting incubation and post-painting purification steps painted viral particles were challenged with human serum for 1 hour at 27° C., as were unpainted viral particles. 48 hours post infection the target HeLa cells (ATCC No. CCL-2) were analysed for infection by flow cytometry. Infectivity of unpainted viral particles was reduced to about 16% after challenging with human serum, compared to not challenged viral particles. The observed infectivity loss in painted viral particles was less pronounced (to 60%), as expected if serum protection from CD59his takes place.

FIG. 4: Varying amounts of GPI-anchored proteins and viral particles. Varying amounts of CD59his (1×, 4×, 16× relative amounts) were incubated with the same amount of viral particles (2× relative amount). After post-painting purification steps immunoblots for CD59 show more association of CD59his to viral proteins when higher concentrations of CD59his were used as starting material. When the same concentration of CD59his was used to paint different amounts of viral particles (1×, 2×, 4× relative amounts) a medium concentration of viral particles seemed to perform best (2× relative amount).

FIG. 5: Painting of feline herpesvirus 1 (FHV-I):

Concentrated supernatants from CrFK cells infected with FHV-I or treated with hygromycin were used in a painting experiment, along with cell culture medium—incubation was carried out in the presence or absence of CD59his for 20 hours before post-painting purification by ultracentrifugation. Immunoblot using specific antibodies directed against CD59 were carried out. Signals can be detected for samples incubated in the presence of CD59 from supernatants from infected (CrFK−FHV+) and—to a lesser degree—hygromycin-treated cells (lanes CrFK−Hyg+). To determine activity of virus post-painting, aliquots of samples were used to infect CrFK cells. The cell destruction or cytopathic effect (CPE) was analysed 24 hours post infection by phase contrast light microscopy. Strong CPE was detected in samples containing FHV-I particles only (CrFK−FHV− and +, respectively). This indicates that virus remains infectious during the procedure. Cytopathic effects (CPE) upon infection of CrFK cells with painted FHV-I particles. In the presence of complete, biologically active virus CrFK cells are infected and damaged (see lane FHV). After painting CPE can be detected in cells infected with the CrFK−FH V samples only, confirming presence of active virus post-painting (see lanes CrFK−FHV− and +). A confluent monolayer is observed in samples not containing viral particles (Medium−/+; CrFK−/+).

FIG. 6: Painting with GPI-anchored green fluorescent protein.

Lentiviral particles derived from STAR producer cells were incubated with GPI-anchored monomeric green fluorescent protein (mGFP-GPI). Post-painting samples were purified by ultracentrifugation and analysed by immunoblotting for presence of mGFP-GPI (upper panel) and p24 (lower panel). mGFP-GPI was only present when viral particles were present, and the sample had been treated by painting with mGFP-GPI (lane VP+) and to a lesser extent when supernatant from non-virus producing parental cells was treated by painting (lane PC+) due to the presence of lipid vesicles of non-viral origin.

FIG. 7: Magnetic nanoparticles (MNP) associate specifically with recombinant GPI proteins GPI-anchored green fluorescent protein was mixed with magnetic nanoparticles (Nickel-NTA-coated iron core particles, average size 5-10 nm). MNPs associated with the target proteins could be retained during three washing procedures after magnetic manipulation (lane B). Most of cellular protein was lost (compare lanes B and A, bottom panel, Coomassie-stained gel), whereas a comparatively large proportion of the target protein stayed associated throughout the process (compare lanes B and A, top panel, immunoblot for GFP). This indicates that magnetic manipulation of GPI-anchored proteins is possible when using magnetic nanoparticles. Lane M exhibits the molecular weight marker.

EXAMPLES

Example 1: Production of CD59his

CrFKCD59hisneo cells expressing the recombinant CD59his were derived from parental CrFK cells by lipofection using lipofectin reagent according to manufacturer's instructions (Invitrogen) with pCD59hisneo. For generation of pCD59hisneo a PCR fragment derived from cDNA (using primers CD59(2)FKHindIII 5'-cacgacaagcttaccatgggaatc-caaggaggg tctgtcctgtt-3 SEQ ID No: 5) and CD59(2)RA-paI5'-atgacgggcccttagggatgaaggctccaggctgctgccagaa-3' SEQ ID No: 6) from HEK293 cells was cloned into the expression vector pcDNA3 (Invitrogen). The his-tag was introduced by a two-step mutagenesis PCR protocol, using first two primer pairs (CD59(2)FKHindIII & CD59RHis 5'-gtgatggtgatggtgatggctatgacctgaatggcagaag-3' SEQ ID No: 8; CD59FHis 5'-catcaccatcaccatcacctgcagtgctacaactgtc-cta-3' SEQ ID No: 7 and CD59(2)RApaI) in two different PCR reactions. Subsequently a mix of both primary fragments was hybridized and amplified using primers CD59(2) FKHindIII and CD59(2)RApaI. The fragment was recloned into pCDNA3 using the HindIII and ApaI sites. 293gpalfp-pLXSNeGFP are derived from HEK293 cells (Ikeda (2003); Klein (1997); Pambalk (2002)). STAR-A-HV (Wilhelm (2007)) are derived from HEK293T cells.

Example 2: Purification of CD59his 4-6 confluent T175 flasks of CrFKCD59hisneo were harvested by scraping after washing cells with 10 ml PBS. Cells were scraped into a total of 25 ml sample application buffer (50 mM TrisHCl, 50 mM NaCl, 35 mM Imidazole, 0.5% sodium deoxycholate, 1% NP40, pH 7.4). 80 µl of protease inhibitor complex (Sigma) was added before sonification of samples for 30 seconds. Samples were incubated for 30 minutes on ice before centrifugation for 30 minutes at 2000 g. Samples were filtered through 0.2 µm filters (Sarstedt) before application to a ÄktaPrime plus FPLC device (GE Healthcare). Prepacked 5 ml HisTrap FF Crude columns (GE HealthCare) were used. Samples were washed using washing buffer (50 mM TrisHCl, 50 mM NaCl, 35 mM Imidazole, pH 7.4) and eluted from columns by elution buffer (50 mM TrisHCl, 50 mM NaCl, 600 mM Imidazole, pH 7.4). Fractions were collected during elution. Presence of CD59his in fractions was determined by immunoblotting. Positive fractions were pooled and concentrated by ultrafiltration using Amicon Ultra filter devices (Millipore, 5 kD molecular weight cut-off). Samples were washed twice with 5 ml painting buffer (50 mM TrisHCl, 50 mM NaCl, pH 7.4). Concentrations were measured using the DC protein assay (BioRad).

Example 3: Painting of Virus with CD59his

Supernatants from the stable lentiviral producer cell line STAR-A-HV (14) or the MLV-based retroviral producer cell line 293gpalfpLXSNeGFP (15, 16, 17) were harvested, filtrated through 0.45 µm filters (Sarstedt) and viral particles were concentrated by ultracentrifugation (2 hrs, 20 000 rpm, 4° C.) in a Beckmann XL-70 ultracentrifuge using a SW28 rotor and resuspended in DMEM cell culture medium (Gibco), before incubation with CD59his at final concentrations between 20 and 100 ng/µl for 21-24 hours at 37° C. and 5% $CO_2$. For painting, supernatants derived from concentration of 2-6 T175 culture flasks were incubated with purified protein at final concentrations between 20 and 100 ng/µl or painting buffer alone. Incubation was carried out at 37° C., 5% CO2 under constant shaking. Incubation times were 3 (infection experiments) to approximately 21 hours (standard experiments). To separate potentially painted virus from free GPI-linked proteins, samples were diluted by addition of 34 ml of DMEM and ultra-centrifuged (2 hrs, 20 000 rpm, 4° C.). To allow for the differentiation between recombinant CD59his and endogenous CD59 present on virus producer cells, samples were subjected to purification with Ni-magnetic particles (MagneHis kit, Promega) after painting according to the instructions of the supplier. and ultracentrifugation to remove endogenous CD59 derived from producer cells (for an overview of procedure see FIG. 1A). CD59his was detected only in samples containing virus and purified CD59his, suggesting that both constituents are necessary (FIG. 1B, lane VP+). No influence on painting was observed as a result of the used media (FIG. 1B, lane ME−) or the parental (non-virus producing) cells (FIG. 1B, lane PC+) used. However, if cells undergo considerable stress i.e. overgrowing in culture prominent amounts of non-viral membrane vesicles can be shed (18) leading to the potential for painting of these exosomal bodies as well. In addition, post-painting procedures were sufficient to remove unpainted CD59his (seen by the absence of a signal for CD59his in the ME+ sample, FIG. 1B) as well as endogenous CD59 (seen by the absence of a signal for CD59his in the PC− sample, FIG. 1B).

Proteins may however stick to viral envelopes regardless of GPI-anchoring in a non-specific manner. Silver staining of painted samples before and after purification via ultracentrifugation showed that the majority of proteins are removed in the purification step (FIG. 1C). In addition, we added rat IgG at the same levels as CD59his to the painting reaction. IgG was not retained by the virus as the CD59his was (FIG. 1C). This indicates that the process is at least semi-specific. Potentially proteins with pronounced hydrophobic stretches e.g. trans-membrane proteins could interact in a way similar to GPI proteins with lipid membranes.

Optimisation was carried out to determine the minimal incubation time necessary for membrane re-insertion. Preliminary results suggested that an incubation time of 3 hours is sufficient for maximal viral painting. Using the minimal incubation time, painting experiments were repeated, to assess infectivity of painted virus. HeLa (ATCC No. CCL-2) cells are infected with painted virions and analysed by flow cytometry 36 hours post infection. Supernatant after infection was collected and analysed for CD59his to confirm painting. (FIG. 2). Painted virus remains infectious, however at reduced levels. Differences in infectivity between samples that received CD59his and mock-painted samples that did not receive GPI proteins are small (FIG. 2, compare samples HV− and HV+). The difference of infectivity to samples before painting was comparatively large (approximately 15-fold, FIG. 2, compare samples HV, HV− and HV+). This indicates that the reduction in infectivity is rather a result of the duration of the process than the process itself.

Example 4: Painting Stoichiometry

Calculations of the stoichiometry of the viral painting process, especially the numbers of GPI proteins incorporated per virus are based on viral titers determined by product enhanced reverse transcriptase (PERT) and by determination of viral painting efficacy from immunoblots. The density of CD59 per virion is defined as the number of total associated molecules $N_{MA}$ divided by the number of virions $N_V$, determined by product enhanced reverse transcriptase (PERT) assay. The PERT assay was carried out as described in (19). Before electroblotting (1.1 mA/cm$^2$) onto PVDF membranes (Hybond P, GE HealthCare). samples were electrophoretically separated on pre-cast 4-12% gradient gels (NuPage, Invitrogen). Monoclonal antiCD59 was purchased from Serotec. Mouse anti human HIV-1 p24 was purchased from Polymun Scientific (Vienna). MLV anti capsid antibody was purified by Biomedica. HRP-conjugated anti-rat and anti-mouse secondary antibodies were purchased from DakoCytomation. Signal detection was carried out using the ECLplus kit (GE HealthCare)

The density (D) of CD59his molecules per virion is dependent on the amount of CD59his (M [g]), the efficacy of the association process ($E_A$) and the number of virions ($N_v$), determined by product enhanced reverse transcriptase (PERT) assay. The constant factor k contains the parameters supposed to not change between experiments, such as the molecular weight ($M_w$) of the GPI protein (20 kDa), the efficacy of purification ($E_p$) and the Avogadro number ($N_a$). Following formula can be used for calculation of the stoichiometry:

$$k=(E_p \times N_a)/(M_w \times 10E9); D=k \times (M \times E_A)/N_v$$

Figure 4:
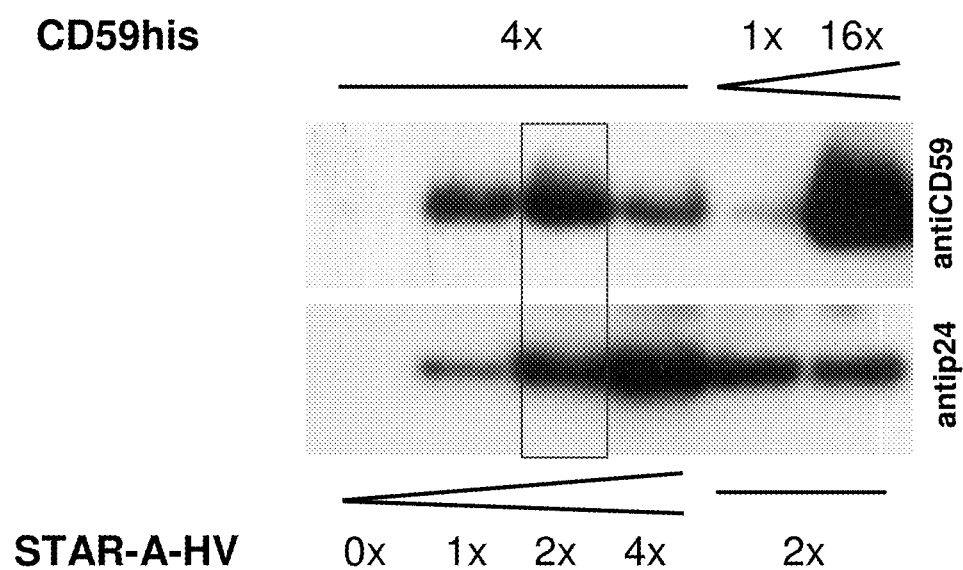
Figure 5:
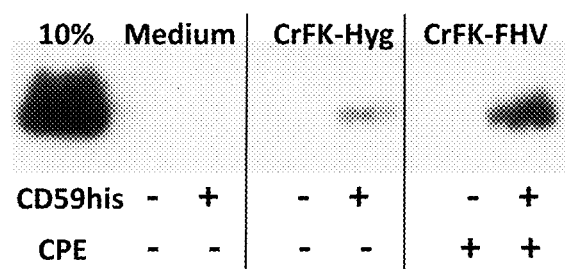
Figure 6:
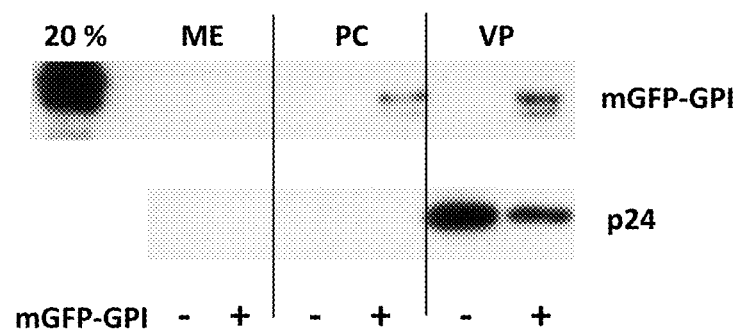

Results for the experiments depicted in FIG. 1B suggested that between 5 and 250 molecules can be found per virus. Experiments carried out using either the same concentration of CD59his on varying viral concentrations or vice versa showed that the amount of incorporation of CD59his into viral envelopes is dependent on viral titers and CD59his concentration (see FIG. 4), whereas the number of inserted CD59his molecules increase with increased amounts of CD59his. In parallel the infectivity of the viral particles decrease with increased numbers of inserted CD59his due to a steric hindrance of natural viral envelope proteins. The best relation between the number inserted compounds and infectivity can be achieved with 50 to 150 CD59his molecules per virion.

Example 5: Infection of HeLa Cells and Flow Cytometry

For infection 8-9×10$^5$ HeLa target cells (ATCC No. CCL-2) were seeded 6 hours prior to infection in 6 well plates. Virus supernatants after post-painting ultracentrifugation were diluted to 1 ml with DMEM supplemented with 10% FCS (Gibco) and 10 µl/ml polybrene (0.8 µg/µl). After 36 hours Supernatants were saved for analysis of CD59his content. Cells were trypsinised, fixed, washed 2 times in PBS and analysed for expression of eGFP in a FACsCalibur flow cytometer (BectonDickinson) using CellQuest software.

Example 6: Painting of Feline Herpesvirus 1 (FHV-I)

Crandell feline kidney cells (CrFK, ATCC No. CCL-94) were infected with FHV-I (2 ml concentrated suspension per T 175 flask) and incubated until complete destruction of cells took place (approximately 48 hours). In parallel, the same amount of CrFK cells was treated with hygromycin (Invitrogen, 200 µg/ml final concentration) to simulate the cell damage usually associated with FHV infection. The supernatants were harvested by ultracentrifugation (2 hrs, 2OK rpm, 4° C. SW28 rotors, using an Beckman XL-70 ultracentrifuge) 48 hours post infection and resuspended in DMEM w/o FCS (Invitrogen). Both concentrated supernatants as well as the same amount of just DMEM w/o FCS were incubated for 20 hours in the presence or absence of purified CD59his (Final concentration up to 100 ng/µl, see example 1 and 2 for production and purification of CD59his)) at 37° C. under constant shaking. Viral particles were separated from not associated CD59his by ultracentrifugation as described above. The samples were then resuspended in DMEM w/o FCS post ultracentrifugation and aliquots used for immunoblotting (to assess association of CD59 to viral particles) or infecting confluent layers of CrFK cells kept in DMEM w/o FCS (to assess presence of viral particles post-painting by determining the cytopathic effect—CPE).

Example 7: Production of mGFP-GPI

To achieve expression of mGFP-GPI the sequence coding for the monomeric GFP as described by Zacharias et al (Zacharias (2002) was cloned into a vector backbone (pcDNA3.1hyg+ (Invitrogen)) providing the his-tag and the GSS of human decay accelerating factor (DAF, CD55) in a 2 step mutational PCR protocol, similar to the one explained in example 1. To primer sets were used: MEHindIIIF (5'-cgcgcgcaagcttaatcaaaacatggctcagcggatgaca-3') SEQ ID No: 1 and MonoHisEG3R (5'-gtggtggtgatggtggtgcttgtaca-gctcgtccatgccgagagt-3') SEQ ID No: 2 in the first set; HisEG1F (5'-caccaccatcaccaccacccaaataaaggaagtggaacc-3') SEQ ID No: 3 and EGApaIR (5'-gaatagggccctaagtcagcaagc-ccatg-3') SEQ ID No: 4 in a second set. Primers MEHindIIIF and EGApaIR were then used to amplify the complete sequence. The fragment was cloned into pcDNA3.1hyg+ (Invitrogen) using the unique HindIII and ApaI sites. Transfection ofHEK293 cells was carried out as described in example 1. Purification and concentration of mG FP-GPI were carried out as described in example 2.

Example 8: Painting with Green Fluorescent Protein (GFP) Variant Proteins

Viral particles were harvested from STAR cells (Ikeda et al. (2003)) as described previously (see example 3). Proteins were purified and concentrated as described previously (see example 2). Cell culture supernatants were concentrated as described previously (see example 3). Purified proteins were incubated with supernatant derived from 4 T 175 flasks per sample at final concentrations up to 100 ng/µl protein. Painting reaction was allowed to commence for 20 hours at 37° C. under constant shaking before ultracentrifugation (as described previously, example 3). No magnetic pre-purification was necessary, as no endogenous GFP can contaminate the samples.

Example 9: Detection of CD59 and mGFP-GPI

Samples were separated on precast 4-12% gradient gels (Invitrogen) under non-denaturing conditions in MES buffer at 100 V. Electroblotting onto PVDF membranes (GE Healthcare) was carried out at 1.1 mA/cm2 for 1 hour. Membranes were blocked overnight in 4% milk powder and 1% bovine serum albumin (Sigma-Aldrich) dissolved in TTBS (5% v/v Tween 20, 150 mM NaCl, 20 mM TrisHCl pH 8.0). Primary antibodies for CD59 (Serotec), p24 (Polymun) and EGFP (Invitrogen) were used at dilutions of 1:2000 and 1:1000 (EGFP), respectively. Secondary antibodies conjugated to horse radish peroxidase (DakoCytomation) against mouse and rabbit IgG were used at dilutions between 1:5000 and 1:10 000. Signal detection was carried out using the ECLplus kit (GE HealthCare)

Example 10: Silver Staining of Proteins

Silver staining of protein extracts was carried out as previously described (Shevchenko et al. (1996). In brief: After fixing and washing, the polyacrylamide gels were sensitized in a 0.02% sodium thiosulfate solution for 1 minute. An aqueous 0.1% silver solution was used for the incubation before development in a sodium carbonate/formaldehyde solution. Color development was stopped by washing in 5% acetic acid in water.

Figure 7:
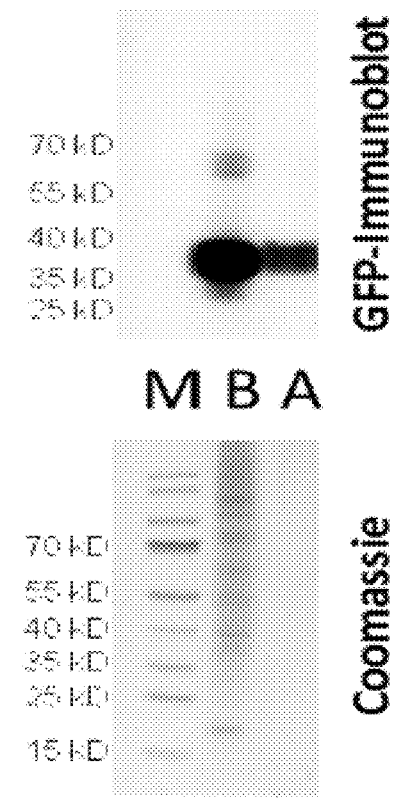

Example 11: Magnetic Nanoparticles (MNP) Associate Specifically with Recombinant GPI Proteins and Allow Magnetic Manipulation GPI-anchored 6× histidine tagged green fluorescent protein or GPI anchored 6× histidine tagged CD59 was expressed in inHEK293 as described previously (see examples 1 and 7). In brief: after two-step mutagenesis PCR to introduce the 6× His tag resulting plasmids were transfected into HEK293 cells by lipofection (Invitrogen). Total cell extracts from expressing cells were mixed with iron based, phospholipid micelle nickel-nitrilo-acetate coated MNPs (Lim (2006); size of 5-10 nm or 50 nm diameter). For binding to target proteins and isolation, MNPs are added to total protein lysates after sonication and mixed for 4 hours at room temperature, then placed into a magnetic stand (Qiagen) and supernatant collected for further testing. Particles plus protein pellet is washed with wash buffer containing ImM Imidazole in Ix extraction Buffer (0.15M NaCl, 0.05 M Tris pH 7.5, 1% v/v NP40 (Sigma), 0.5% w/v Sodiumdeoxycholate (Sigma) and mixed by pipeting. This process is repeated twice so that three washing steps are performed in total. Bound protein-MNP can be then used for painting experiments or eluted using high concentrations of imidazole (500 mM) (and hence purified for further analysis). Cells were analysed by immunoblots using GFP specific antibodies (Invitrogen) and Coomassie staining of polyacrylamide gels. Levels of cellular protein are dramatically reduced by the purification step (as can be seen in the Coomassie staining, FIG. 7, bottom panel) and a large portion of the total amount target protein is recovered after purification (FIG. 7 lane A), when compared with the complete extract (FIG. 7, lane B)

| Primer used | |
|---|---|
| MEHindIIIF | (5'-cgcgcgcaagcttaatcaaaaca tggctcagcggatgaca-3') SEQ ID No: 1 |
| MonoHisEG3R | (5'-gtggtggtgatggtggtgcttgt acagctcgtccatgccgagagt-S') SEQ ID No: 2 |
| HisEGIF | (5'-caccaccatcaccaccacccaaa taaaggaagtggaacc-3') SEQ ID No: 3 |
| EGApaIR | (5'-gaatagggccctaagtcagcaag cccatg-3') SEQ ID No: 4 |
| CD59(2)FKHindIII | (5'-cacgacaagcttaccatgggaat ccaaggagggtctgtcctgtt-3) SEQ ID No: 5 |
| CD59(2)RApal | (5'-atgacgggcccttagggatgaag gctccaggctgctgccagaa-3') SEQ ID No: 6 |
| CD59FHis | (5'-catcaccatcaccatcacctgca gtgctacaactgtccta-3') SEQ ID No: 7 |
| CD59RHis | (5'-gtgatggtgatggtgatggctat gacctgaatggcagaag-3') SEQ ID No: 8 |

REFERENCES

Beer C. et al. Virol J 22, 36-44 (2005)
Breun, S., et al. BBRC 264, 1-5 (1999).
Brügger, B. et al. Retrovirol 4, 70-82 (2007)
Campbell R E. PNAS 99, 7877-7882 (2002)
Chan, L., et al. J. Virol 79(20), 13190-13194 (2005).
Hlavaty, J., et al. J. Virol 78(3), 1384-1392 (2004).
Ikeda, Y., et al. Nature Biotechnology 21, 569-572 (2003).
Ito, A, et al. J. Bioscience and Bioengineering 100 (1), 1-11 (2005)
Jordan, A, et al. J Neuro-O neology 78, 7-14 (2006)
Keler, T, et al., Oncogene 26, 3758-3767 (2007),
Klein, D. et al. Gene Therapy 44, 1256-1260 (1997).
Kueng, H J et al. J. J. Virol. 81(16), 8666-8676 (2007).
Legler, D. F., et al FASEB J. 19, 73-75 (2005).
Lim Y T et al. Biochem Biophys Res Commun 344 926-30 (2006)
McHugh, R. S. Proceed. Natl. Acad. Sci. USA 92, 8059-8063 (1995).
Medof, M. E et al., FASEB J. 10, 574-586 (1996).
Metzner et al. FASEB J. 22, 2734-2739 (2008)
Metzner et al. Virol 382, 125-131 (2008)
Morandat, S., et al. Biochim. Biophys. Acta 1564(2), 473-478 (2002).
Pambalk, K., et al. BBRC 293, 239-246 (2002).
Paulick, M G et al. J. Am. Chem. Soc, 129:11543-11550 (2007)
Premkumar, D. R. D.; et al. J. Cell. Biochem. 82, 234-245 (2001).
Rohrbach, F et al., 2005, J. Immunol 174 5481-5489 (2005). 174:5481-9).
Ronzon, F., et alj. Membr. Biol. 197(3), 169-177 (2004).
Roux, P et al. Proc. Natl. Acad. Sci. 86, 9079-9083 (1989)
Schevchenko, A et al. Anal. Chem. 68, 850-858 (1996)
Skountzou, L, et al J. Virol. 81(3), 1083-1093 (2007).
Steinrigl, A, et al. Virology 362(1), 50-9 (2007)
Taraboletti, G., et al. Neoplasia 8(2) 96-103 (2006).
Wilhelm, C et al. J Nanosci Nanotechnol 7, 2933-2937 (2007)
Yang, H et al. Biotechnol. Bioeng. 101, 357-68 (2008)
Yang, L et al. Proc. Natl. Acad Sci. USA 103, 11479-84 (2006)
Yang, L et al. Nat. Biotechnol. 26(3), 326-34 (2008) Zacharias D A Science 296, 913-916 (2002)
Zaccharias D A Science's STKE 131, PE23 (2002)
Ziegler, L et al. Hum Gene Ther. 19(9), 861-72 (2008)

The invention claimed is:

1. A method of stimulating an immune response or immunomodulation of a subject, the method comprising:
   a) incubating a fluid containing enveloped viral particles with one or more reactants consisting of a hydrophilic target domain and a lipophilic membrane anchor domain, wherein the lipophilic membrane anchor domain becomes integrated into the lipid double layer of the envelope of the viral particle, wherein the hydrophilic target domain becomes exposed to the fluid, wherein the hydrophilic target domain is selected from the group consisting of polysaccharides, nucleic acids, dyes, radioactive ligands, fluorescent dyes, synthetic beads, magnetic particles and proteins or polypeptides comprising a protein tag;
   b) separating enveloped modified viral particles from excessive reactants; and
   c) administering to the subject the modified enveloped viral particle.

2. The method according to claim 1, wherein the viral particle is selected from the group consisting of a wild-type virus, an attenuated virus, an empty virus particle and a genetically modified viral vector.

3. The method according to claim 1, wherein the viral envelope has a protein to lipid ratio between 50:50 and 90:10 mol %.

4. The method according to claim 1, wherein the lipophilic membrane anchor domain is selected from the group consisting of phospholipid-polyethyleneglycol, stearyl, palmityl, myristyl, cholesterol, chelator lipid nitrilotriacetic acid ditetradecylamine (NTADTDA) and glycosylphosphatidylinositol (GPI).

5. The method of claim 1, wherein the protein is an immuno-stimulatory protein.

6. The method according to claim 1, wherein the protein or the polypeptide is an enzyme, an antibody, a receptor, a marker protein, a fluorescence protein, a complement inhibitor or a cytokine.

7. The method according to claim 1, wherein the enveloped viral particle is selected from the group consisting of Arenaviridae, Bunyaviridae, Coronaviridae, Filoviridae, Flaviviridae, Hepadnaviridae, Herpesviridae, Orthomyxoviridae, Paramyxoviridae, Poxviridae, Retroviridae, Rhabdoviridae and Togaviridae.

8. The method according to claim 1, wherein the enveloped viral particle is one of a retrovirus, a poxvirus, a herpesvirus, an influenza virus and a lentivirus.

9. The method according to claim 8, wherein the enveloped viral particle is one of a mouse leukemia virus, a feline herpesvirus and a vaccinia virus.

10. The method according to claim 1, wherein the enveloped viral particle comprises a genetically modified genome compared to its wild-type form.

11. The method of claim 1, comprising prior to step a) the step of obtaining enveloped viral particles from a suspension fluid.

12. A method of treating a subject, the method comprising:
   a) incubating a fluid containing enveloped viral particles with one or more reactants consisting of a hydrophilic target domain and a lipophilic membrane anchor domain, wherein the lipophilic membrane anchor domain becomes integrated into the lipid double layer of the envelope of the viral particle, wherein the hydrophilic target domain becomes exposed to the suspension fluid, wherein the hydrophilic target domain is selected from the group consisting of polysaccharides, nucleic acids, dyes, radioactive ligands, fluorescent dyes, synthetic beads, magnetic particles and proteins or polypeptides comprising a protein tag;
   b) separating enveloped modified viral particles from excessive reactants; and
   c) administering to the subject the modified enveloped viral particle.

13. The method according to claim 12, wherein the viral particle is selected from the group consisting of a wild-type virus, an attenuated virus, an empty virus particle and a genetically modified viral vector.

14. The method of claim 12, wherein the treatment is selected from the group consisting of gene-therapy, vaccination and immunomodulation.

15. The method of claim 12, comprising prior to step a) the step of obtaining enveloped viral particles from a suspension fluid.

16. A method of modifying at least one enveloped viral particle and detecting the modified enveloped viral particle, the method comprising:
   a) incubating a fluid containing enveloped viral particles with one or more reactants consisting of a hydrophilic target domain and a lipophilic membrane anchor domain, wherein the lipophilic membrane anchor domain becomes integrated into the lipid double layer of the envelope of the viral particle, wherein the hydrophilic target domain becomes exposed to the fluid, wherein the hydrophilic target domain is selected from the group consisting of polysaccharides, nucleic acids, dyes, radioactive ligands, fluorescent dyes, synthetic beads, magnetic particles and proteins or polypeptides comprising a protein tag;

b) separating enveloped modified viral particles from excessive reactants;

c) contacting one of a cell, a tissue and a subject with a modified enveloped viral particle; and d) detecting the modified enveloped viral particle bound to the cell, tissue or subject.

* * * * *